United States Patent [19]
Goebel et al.

[11] Patent Number: 6,049,076
[45] Date of Patent: Apr. 11, 2000

[54] ION MOBILITY SPECTROMETER

[75] Inventors: Johann Goebel; Ulrich Breit, both of Munich, Germany

[73] Assignee: Daimler-Benz AG, Germany

[21] Appl. No.: 08/985,903

[22] Filed: Dec. 5, 1997

[30] Foreign Application Priority Data

Dec. 5, 1996 [DE] Germany .................. 196 50 419

[51] Int. Cl.$^7$ .................. H01J 49/40; B01D 59/44
[52] U.S. Cl. .................. 250/286; 250/287
[58] Field of Search .................. 250/286, 287

[56] References Cited

U.S. PATENT DOCUMENTS 4,777,363 10/1988 Eiceman et al. .................. 250/286
5,834,771 11/1998 Yoon et al. .................. 250/286

*Primary Examiner*—Edward P. Westin
*Assistant Examiner*—Nikita Wells
*Attorney, Agent, or Firm*—Evenson, McKeown, Edwards & Lenahan, P.L.L.C.

[57] ABSTRACT

An ion mobility spectrometer has an ionization chamber, drift chamber, and a system for generating an electrical field in the drift chamber. The system for generating the electrical field comprises a plurality of capacitors that are connected together in parallel for charging and are connected in series for generating a high-voltage.

5 Claims, 1 Drawing Sheet

IF SWITCHES (SW) ARE IN PHASE

Ø1   CAPACITORS ARE CONNECTED IN PARALLEL FOR CHARGING

Ø2   CAPACITORS ARE CONNECTED IN SERIES FOR GENERATING A HIGH VOLTAGES

ION MOBILITY SPECTROMETER

BACKGROUND AND SUMMARY OF THE INVENTION

This application claims the priority of German patent document 196 50 419.8, the disclosure of which is expressly incorporated by reference herein.

The present invention relates to an ion mobility spectrometer (IMS) with an ionization chamber, a drift chamber, an ion collector located in the drift chamber, and a device, connected to a high-voltage source, to generate an electrical field in the drift chamber.

To operate an ion mobility spectrometer (IMS) a high voltage, in the vicinity of more than 1000 V, is required to create the necessary electrical field (usually 300 V/cm) in the drift chamber. The potential is usually dropped through one or more resistances, and potential control can be effected by a resistance layer or potential-guiding conductors connected with one another by resistances.

In addition to the ionization chamber, drift chamber and ion collector, a typical ion mobility spectrometer has a lattice-shaped gate between the Ionization chamber and the drift chamber, with the ions migrating in drift chamber toward the ion collector under the influence of the electrical field. The drift time is different for different ions, and is determined by their mobility in the gas atmosphere of the drift chamber.

The field can be formed by equidistant metal rings separated from one another by insulating rings and connected electrically with one another by resistances. One end of this system is connected to a high-voltage source, which is usually in the kV range, while the other end is connected to ground.

It is conventional for the high-voltage source to supply voltage continuously, and the current flowing through the resistances thus has a considerable power requirement, in the vicinity of 10 watts. The size of the high-voltage generator according to the prior art therefore has prevented miniaturization of an IMS.

Another disadvantage lies in the fact that the high-voltage circuit is active during measurement, so that extensive shielding is necessary in order to prevent interference during measurement of the ion current (which is in the vicinity of $10^{-12}$ Amps).

An example of an IMS of this kind is described in U.S. Pat. No. 4,777,363. The drift chamber is equipped with a plurality of metal cylindrical rings, which are charged with a corresponding drift voltage by a plurality of resistances connected in parallel. The rings are also separated electrically from one another by suitable insulating layers.

One object of the present invention is to provide an ionization mobility spectrometer in which the electrical power requirement is considerably reduced during the generation of high voltage.

Another object of the invention is to provide an ion mobility spectrometer in which the high-voltage part itself is considerably reduced in size.

Still another object of the invention is to provide such an ion mobility spectrometer in which interference is reduced.

These and other objects and advantages are achieved by the ion mobility spectrometer according to the invention, in which the system for generating an electrical field has several capacitors which are connected in parallel with one another for charging, and are connected in series following charging, to generate a high voltage. The system according to the invention has potential-conducting planes to generate the electrical field, said planes being connected with the individual capacitors.

With the high-voltage generation arrangement according to the invention, the electrical power draw can be lowered considerably, and the size of the high-voltage section is minimized as well. The high voltage is then exclusively a DC voltage, so that a battery can be used as the voltage source, which facilitates miniaturization of the IMS.

During the measurement, no current flows in the high-voltage supply itself, so that the previously conventional shielding measures can be completely eliminated.

Other objects, advantages and novel features of the present invention will become apparent from the following detailed description of the invention when considered in conjunction with the accompanying drawings.

DETAILED DESCRIPTION OF THE DRAWINGS

Figure 1:
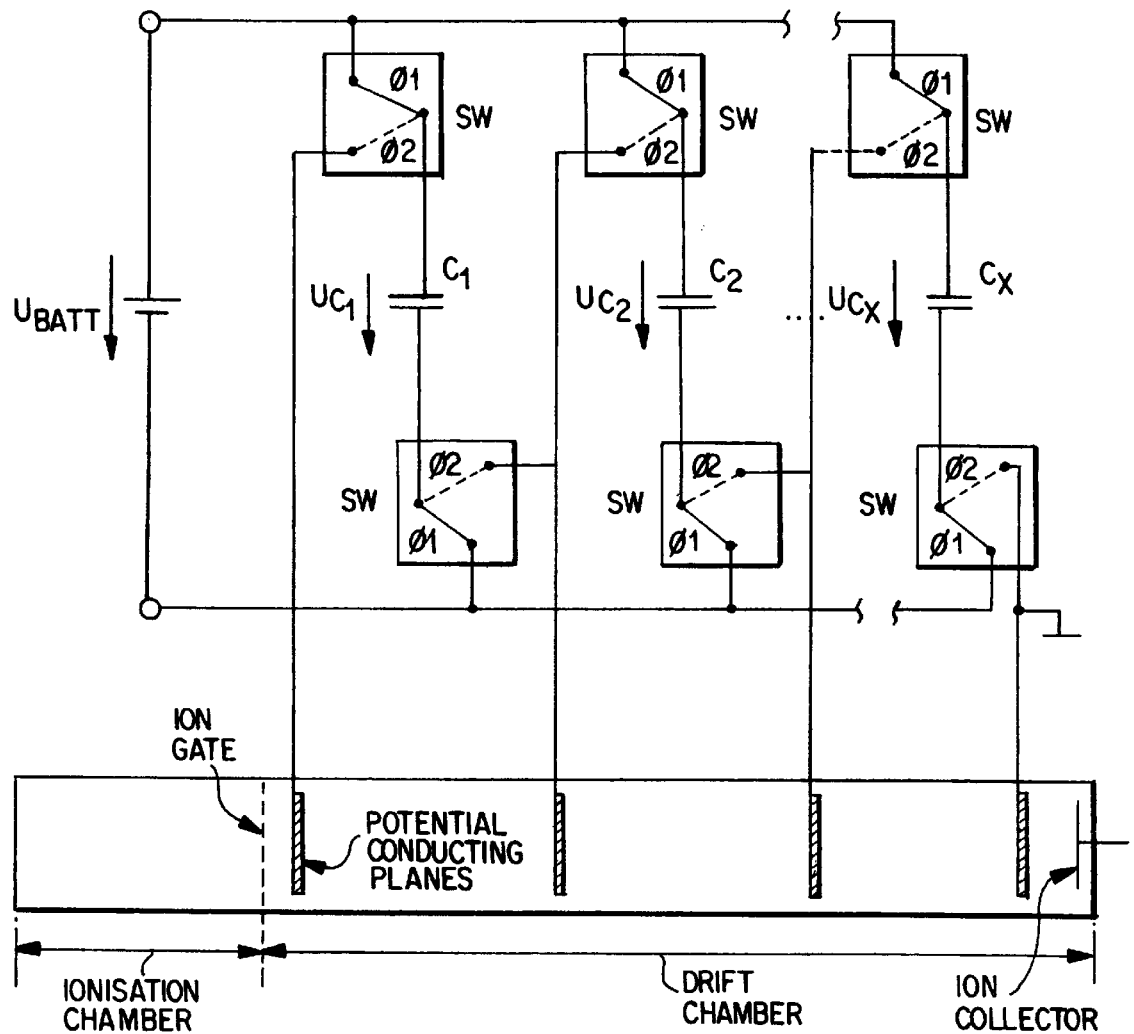
FIG. 1 shows a schematic diagram of a possible circuit for the capacitors for generating high voltage in the test chamber according to the invention.

Phase $\phi 1$ shows the circuit composed of several capacitors in parallel $C_1, C_2, \ldots C_n$, subjected to a battery voltage $U_B$, with the individual capacitors receiving the voltage values $UC_1, UC_2, \ldots UC_n$. After the capacitors have been charged in parallel they are connected in series phase $\phi 2$ in a conventional manner, and connected with the potential-conducting planes of the drift chamber.

According to the invention therefore, the ion mobility spectrometer (IMS) is provided with a high-voltage supply that consists of a plurality of capacitors which are connected in parallel for charging, and are connected in series for generating a high voltage.

During field generation with potential-conducting planes, the capacitors connect these planes, with the voltage difference between the two adjacent planes being generated by the voltages of the capacitors connecting them.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An ion mobility spectrometer comprising:
   an ionization chamber;
   a drift chamber;
   an ion collector located in the drift chamber;
   a high voltage source; and
   a device, connected with the high-voltage source, for generating an electrical field in the drift chamber;
   wherein the high voltage source comprises a plurality of capacitors which are divided into groups consisting of least one capacitor, the groups being connected in parallel with one another for charging, and connected in series for generating a high voltage after they are charged.

2. Ion mobility spectrometer according to claim 1 wherein the high-voltage source includes a battery.

3. Ion mobility spectrometer according to claim 1 wherein the system for generating the electrical field has potential-conducting planes which are connectable with the groups of capacitors.

4. A high-voltage source for an ion mobility spectrometer having an ionization chamber, a drift chamber, and a device which is connected to the high-voltage source for generating an electric field in the drift chamber, said high-voltage source comprising:

a plurality of capacitors;

means for connecting said capacitors in parallel during a charging phase in which the capacitors are charged with a selected voltage value; and means for connecting said capacitors in series and for connecting said series connected capacitors with said device for generating an electric field in the drift chamber during a measurement phase.

5. A method of providing a high-voltage source for operating an ion mobility spectrometer having an ionization chamber, a drift chamber and a device which is connected to the high-voltage source for generating an electric field in the drift chamber, said method comprising:

providing a plurality of capacitors;

connecting the capacitors in a parallel arrangement which is coupled to a voltage supply during a charging phase; and connecting the capacitors in a series arrangement which is coupled with said device for generating an electric field in the drift chamber, during a measurement phase.

* * * * *